United States Patent
Rabindran et al.

(10) Patent No.: US 12,082,887 B2
(45) Date of Patent: Sep. 10, 2024

(54) SYSTEM AND METHOD FOR INTER-ARM REGISTRATION

(71) Applicant: INTUITIVE SURGICAL OPERATIONS, INC., Sunnyvale, CA (US)

(72) Inventors: Dinesh Rabindran, San Jose, CA (US); Simon P. Dimaio, San Carlos, CA (US); Ambarish G. Goswami, Fremont, CA (US); James Zachary Woodruff, Seattle, WA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 245 days.

(21) Appl. No.: 17/790,892

(22) PCT Filed: Jan. 5, 2021

(86) PCT No.: PCT/US2021/012213
§ 371 (c)(1),
(2) Date: Jul. 5, 2022

(87) PCT Pub. No.: WO2021/141902
PCT Pub. Date: Jul. 15, 2021

(65) Prior Publication Data
US 2023/0028689 A1    Jan. 26, 2023

Related U.S. Application Data

(60) Provisional application No. 62/957,537, filed on Jan. 6, 2020.

(51) Int. Cl.
*A61B 34/20* (2016.01)
*A61B 34/35* (2016.01)
*B25J 9/16* (2006.01)

(52) U.S. Cl.
CPC .............. *A61B 34/20* (2016.02); *A61B 34/35* (2016.02); *B25J 9/1697* (2013.01);
(Continued)

(58) Field of Classification Search
CPC ...... B25J 9/1692; B25J 9/1694; B25J 9/1697; G05B 2219/39008; G05B 2219/39016;
(Continued)

(56) References Cited

U.S. PATENT DOCUMENTS

| | | |
|---|---|---|
| 8,521,331 B2 | 8/2013 | Itkowitz |
| 8,935,003 B2 | 1/2015 | Itkowitz et al. |

(Continued)

FOREIGN PATENT DOCUMENTS

| | | |
|---|---|---|
| EP | 3181085 A1 | 6/2017 |
| WO | WO-2019094099 A1 | 5/2019 |
| WO | WO-2019099346 A2 | 5/2019 |

OTHER PUBLICATIONS

Pari et al., "Image Based Visual Servoing: Estimated Image Jacobian by Using Fundamental Matrix VS Analytic Jacobian", 2008, ICIAR 2008, pp. 706-717 (Year: 2008).*

(Continued)

*Primary Examiner* — Spencer D Patton
(74) *Attorney, Agent, or Firm* — Artegis Law Group, LLP (57) ABSTRACT

Systems and methods for inter-arm registration include a computer-assisted system having a control unit coupled to a repositionable arm of a computer-assisted device. The control unit is configured to: receive, from an imaging device, successive images of an instrument mounted to the repositionable arm; determine an observed velocity of a feature of the instrument; determine an expected velocity of the feature of the instrument based on kinematics of the repositionable arm; transform the observed velocity and/or the expected velocity to a common coordinate system using a registration (Continued)

transform; determine an error between directions of the observed and expected velocities in the common coordinate system; and update the registration transform based on the determined error. In some embodiments, the instrument is a medical instrument and the imaging device is an endoscope. In some embodiments, the control unit is further configured to control the instrument using the registration transform.

26 Claims, 4 Drawing Sheets

(52) U.S. Cl.
CPC .................. *A61B 2034/2055* (2016.02); *G05B 2219/39008* (2013.01); *G05B 2219/39022* (2013.01); *G05B 2219/40598* (2013.01); *G05B 2219/40611* (2013.01)

(58) Field of Classification Search
CPC ........... G05B 2219/39022; G05B 2219/39387; G05B 2219/39391; G05B 2219/39395; G05B 2219/40598; G05B 2219/40607; G05B 2219/40611; G05B 2219/40557; A61B 34/20; A61B 34/35; A61B 90/361; A61B 2034/2055
See application file for complete search history.

(56) References Cited

U.S. PATENT DOCUMENTS

| | | | |
|---|---|---|---|
| 8,966,173 | B1 | 2/2015 | Taylor et al. |
| 2011/0208093 | A1 | 8/2011 | Gross et al. |
| 2012/0158179 | A1* | 6/2012 | Ooga ..................... B25J 9/1697 901/47 |
| 2019/0143513 | A1 | 5/2019 | Rabindran et al. |
| 2020/0360097 | A1 | 11/2020 | DiMaio et al. |

OTHER PUBLICATIONS

Cai et al., "6D Image-based Visual Servoing for Robot Manipulators with uncalibrated Stereo Cameras", Oct. 2014, IEEE International Conference of Intelligent Robots and Systems (Year: 2014).*

Qian et al., "Online Estimation of Image Jacobian Matrix by Kalman-Bucy Filter for Uncalibrated Stereo Vision Feedback", May 2002, IEEE International Conference on Robotics & Automation, pp. 562-567 (Year: 2002).*

Sutanto et al., "The role of exploratory movement in visual servoing without calibration", 1998, Robotics and Autonomous Systems 23, pp. 153-169 (Year: 1998).*

Co-pending U.S. Appl. No. 16/763,552, inventors Ambarish; G. Goswami et al., filed on May 12, 2020.

Co-pending U.S. Appl. No. 17/637,060, inventor Parastegari; Sina, filed on Feb. 21, 2022.

International Search Report and Written Opinion for Application No. PCT/US2021/012213, mailed Apr. 30, 2021, 15 pages.

Vertut, J, and Coiffet, P., "Robot Technology: Teleoperation and Robotics Evolution and Development," English translation, Prentice-Hall, Inc., Inglewood Cliffs, Nj, USA 1986, vol. 3A, 332 pages.

Wu L., et al., "Finding the Kinematic Base Frame of a Robot by Hand-Eye Calibration Using 3D Position Data," IEEE Transactions on Automation Science and Engineering, Jan. 2017, vol. 14 (1), pp. 314-324.

International Preliminary Report on Patentability for Application No. PCT/US2021/012213, mailed on Jul. 21, 2022, 09 pages.

* cited by examiner

SYSTEM AND METHOD FOR INTER-ARM REGISTRATION

RELATED APPLICATIONS

This application is a U.S. National Stage patent application of International Patent Application No. PCT/US2021/012213, filed Jan. 5, 2021, the benefit of which is claimed, and claims the benefit of U.S. Provisional Application No. 62/957,537, filed Jan. 6, 2020, each of which is incorporated by reference herein.

TECHNICAL FIELD

The present disclosure relates generally to operation of devices having instruments mounted to repositionable arms of computer-assisted devices and more particularly to determining registration between instruments on different computer-assisted devices.

BACKGROUND

More and more devices are being replaced with computer-assisted electronic devices. This is especially true in industrial, entertainment, educational, and other settings. As a medical example, the hospitals of today with large arrays of electronic devices being found in operating rooms, interventional suites, intensive care wards, emergency rooms, and/or the like. For example, glass and mercury thermometers are being replaced with electronic thermometers, intravenous drip lines now include electronic monitors and flow regulators, and traditional hand-held surgical and other medical instruments are being replaced by computer-assisted medical devices.

These computer-assisted devices are useful for performing operations and/or procedures on materials, such as the tissue of a patient, that are located in a workspace. When the workspace is separated from the operator controlling the computer-assisted device, it is common for the operator to control the computer-assisted device using teleoperation and to monitor the activity of the computer-assisted device using an imaging device positioned to capture images or video of the workspace. In computer-assisted devices with instruments that are mounted to repositionable arms and/or manipulators, the teleoperation typically involves the operator using one or more input controls to provide movement commands for the instruments that are, for example, implemented by driving one or more joints in a respective repositionable arm and/or manipulator. In some computer-assisted devices, one of the instruments may be an imaging device mounted to a repositionable arm so that the operator may change a location and/or a direction of a field of view of the imaging device so as to be able to capture images of the workspace from different positions and orientations.

Because the operator is relying on images of the other instruments captured by the imaging device to teleoperate the other instruments, it is useful to know the geometric relationships (e.g., the registrations) between the imaging device and the other instruments so that movements of the hands of the operator relative to an eye coordinate system of an operator station may be properly translated to motions of the other instruments.

Accordingly, it would be advantageous to have methods and systems to determine registrations between an imaging device and one or more instruments being teleoperated.

SUMMARY

Consistent with some embodiments, a computer-assisted system includes a control unit coupled to a repositionable arm of a computer-assisted device. The control unit is configured to: receive, from an imaging device, successive images of an instrument mounted to the repositionable arm; determine an observed velocity of a feature of the instrument; determine an expected velocity of the feature of the instrument based on kinematics of the repositionable arm; transform the observed velocity, the expected velocity, or both the observed and expected velocities to a common coordinate system using a registration transform; determine an error between a direction of the observed velocity and a direction of the expected velocity in the common coordinate system; and update the registration transform based on the determined error.

Consistent with some embodiments, a method of operating a computer-assisted system using a control unit includes receiving, from an imaging device, successive images of an instrument mounted to a repositionable arm of a computer-assisted device; determining an observed velocity of a feature of the instrument; determining an expected velocity of the feature of the instrument based on kinematics of the repositionable arm; transforming the observed velocity, the expected velocity, or both the observed and expected velocities to a common coordinate system using a registration transform; determining an error between a direction of the observed velocity and a direction of the expected velocity in the common coordinate system; and updating the registration transform based on the determined error.

Consistent with some embodiments, a computer-assisted system includes a control unit coupled to a repositionable arm of a computer-assisted device. The control unit is configured to receive, from an imaging device, successive images of an instrument mounted to the repositionable arm; determine an observed orientation of an alignment feature of the instrument; determine an expected orientation of the alignment feature of the instrument based on kinematics of the repositionable arm; transform the observed orientation, the expected orientation, or both the observed and expected orientations to a common coordinate system using a registration transform; determine an error between the observed orientation and the expected orientation in the common coordinate system; and update the registration transform based on the determined error.

Consistent with some embodiments, a method of operating a computer-assisted system using a control unit includes receiving, from an imaging device, successive images of an instrument mounted to a repositionable arm of a computer-assisted device; determining an observed orientation of an alignment feature of the instrument; determining an expected orientation of the alignment feature of the instrument based on kinematics of the repositionable arm; transforming the observed orientation, the expected orientation, or both the observed and expected orientations to a common coordinate system using a registration transform; determining an error between the observed orientation and the expected orientation in the common coordinate system; and updating the registration transform based on the determined error.

Consistent with some embodiments, a non-transitory machine-readable medium including a plurality of machine-readable instructions which when executed by one or more processors are adapted to cause the one or more processors to perform any of the methods described herein.

In the figures, elements having the same designations have the same or similar functions.

DETAILED DESCRIPTION

This description and the accompanying drawings that illustrate inventive aspects, embodiments, implementations, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of computer-assisted devices and elements in terms of their state in three-dimensional space. As used herein, the term "position" refers to the location of an element or a portion of an element in a three-dimensional space (e.g., three degrees of translational freedom along Cartesian x-, y-, and z-coordinates). As used herein, the term "orientation" refers to the rotational placement of an element or a portion of an element (three degrees of rotational freedom—e.g., roll, pitch, and yaw, angle-axis, rotation matrix, quaternion representation, and/or the like). As used herein, the term "shape" refers to a set positions or orientations measured along an element. As used herein, and for a device with repositionable arms, the term "proximal" refers to a direction toward the base of the computer-assisted device along its kinematic chain and "distal" refers to a direction away from the base along the kinematic chain.

As used herein, the term "pose" refers to the six degree of freedom (DOF) spatial position and orientation of a coordinate system of interest attached to a rigid body. As used herein, the term "feature" refers to a fixed point, alignment axis and/or similar geometrical element, either measured directly using an imaging device or derived from such measurements using mathematical models.

As used herein, the terms "observed feature" or "primary feature" refer to a feature that is measured or detected directly by an imaging device; and the terms "derived feature," "secondary feature," or "computed feature" refer to a feature that is estimated or computed from a measured feature using mathematical models. A collection of one or more features, primary and/or secondary, is termed a feature set.

Aspects of this disclosure are described in reference to computer-assisted systems and devices, which may include systems and devices that are teleoperated, remote-controlled, autonomous, semiautonomous, robotic, and/or the like. Further, aspects of this disclosure are described in terms of an implementation using a surgical system, such as the da Vinci® Surgical System commercialized by Intuitive Surgical, Inc. of Sunnyvale, California. Knowledgeable persons will understand, however, that inventive aspects disclosed herein may be embodied and implemented in various ways, including robotic and, if applicable, non-robotic embodiments and implementations. Implementations on da Vinci®

Surgical Systems are merely exemplary and are not to be considered as limiting the scope of the inventive aspects disclosed herein. For example, techniques described with reference to surgical instruments and surgical methods may be used in other contexts. Thus, the instruments, systems, and methods described herein may be used for humans, animals, portions of human or animal anatomy, industrial systems, general robotic, or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

Figure 1:
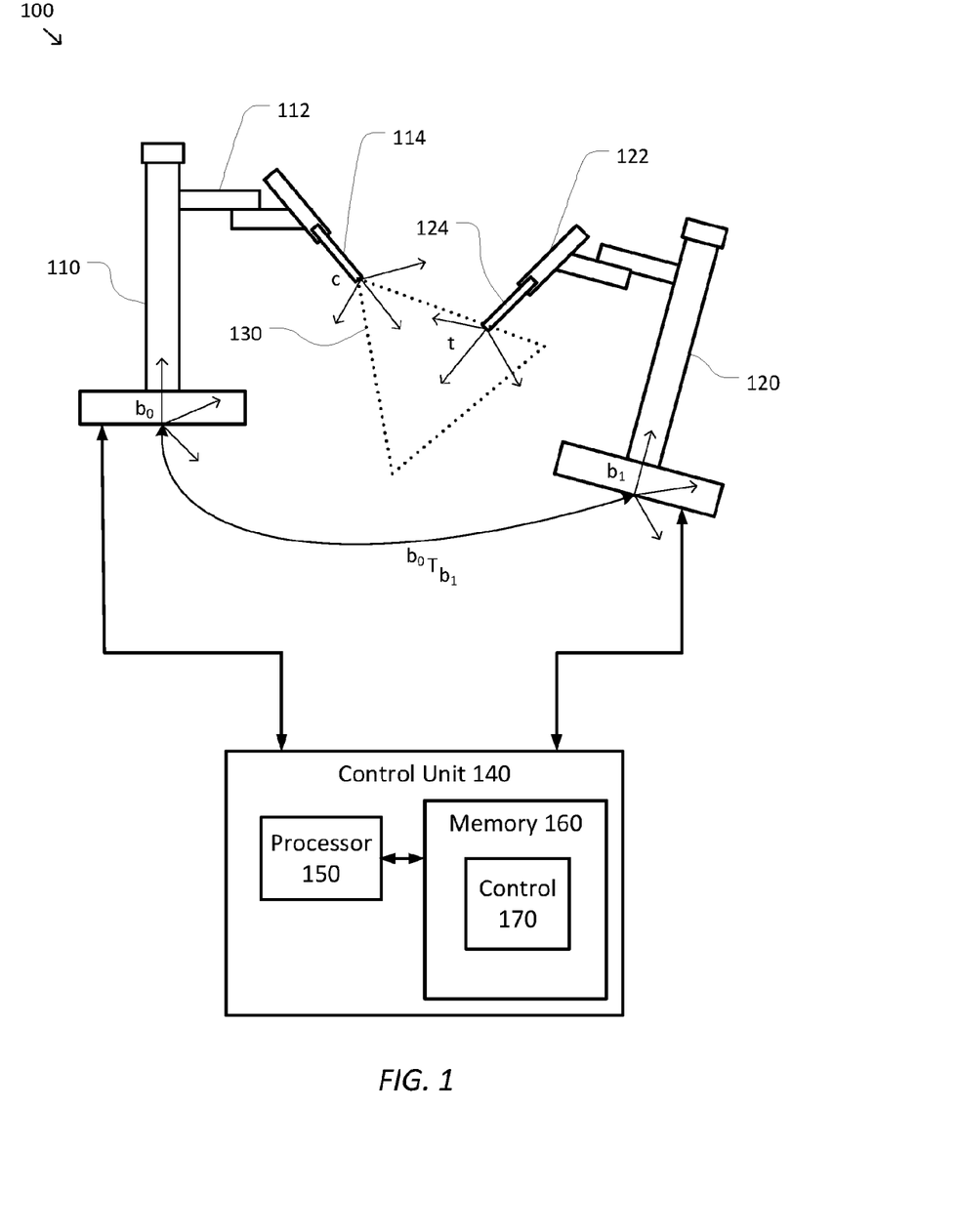
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes two computer-assisted devices 110 and 120. Computer-assisted device 110 includes a repositionable structure having a repositionable arm 112 configured to support an instrument. The instrument may be an imaging instrument, a manipulation instrument, an irrigation or suction instrument, or any other appropriate instrument. In the example of FIG. 1, instrument comprises an imaging device 114. In some examples, the instrument comprises an imaging device 114 that is a monoscopic or stereoscopic camera, a still or video camera, an endoscope, a hyperspectral device, an infrared or ultrasonic device, an ultrasonic device, a fluoroscopic device, and/or the like. Similarly, computer-assisted device 120 includes a repositionable structure having a repositionable arm 122 configured to support an instrument 124. In some examples, instrument 124 may be an imaging device, a non-imaging device, and/or the like. In some medical examples, the instrument may be a medical instrument, such as forceps, clip appliers, a gripper, a retractor, a cautery instrument, a suction instrument, a suturing device, a stapling device, a cutting device, and/or the like. In some examples, instrument 124 may include an end effector capable of performing multiple tasks, such as both grasping a material (e.g., tissue of a patient) located in the workspace and delivering energy to the grasped material. In some examples, the energy may include ultrasonic, radio frequency, electrical, magnetic, thermal, light, and/or other types of energy. In some examples, each of repositionable arm 112, repositionable arm 122, imaging device 114, and/or instrument 124 may include one or more joints. In some medical examples, imaging device 114 and/or instrument 124 may be inserted into a workspace (e.g., anatomy of a patient or cadaver, a veterinary subject, an anatomical model, and/or the like) through a respective cannula, access port, and/or the like. In some embodiments, computer-assisted system 100 may be found in an operating room and/or an interventional suite.

FIG. 1 also shows a field of view 130 of imaging device 114 by indicating a region within the workspace where imaging device 114 may capture images of the workspace and objects and events within the workspace. In the configuration shown in FIG. 1, at least a distal portion of instrument 124 is located within field of view 130, allowing imaging device 114 to capture images of at least the distal portion of instrument 124 when instrument 124 is not visually obstructed completely from imaging device 114. According to some embodiments and as described further below, images of instrument 124 obtained by imaging device 114 may be used to determine a registration transform between computer-assisted device 110 and computer-assisted device 120.

FIG. 1 also shows various coordinate systems that are useful in describing how the registration transform is determined. Coordinate system $b_0$ corresponds to a base coordinate system of computer-assisted device 110. In some examples, coordinate system $b_0$ may have its origin located at a central point on a base of computer-assisted device 110 and may be aligned with one or more major axes of computer-assisted device 110. In some examples, the central point on the base of computer-assisted device 110 may be on a level, planar surface on which computer-assisted device 110 may be wheeled, slid, and/or otherwise repositioned. In some examples, a z-axis of coordinate system $b_0$ may correspond to a vertical up direction. Similarly, coordinate system $b_1$ corresponds to a base coordinate system of computer-assisted device 120. In some examples, coordinate system $b_1$ may have its origin located at a central point on a base of computer-assisted device 120 and may be aligned with one or more major axes of computer-assisted device 120. In some examples, the central point on the base of computer-assisted device 120 may be on a level, planar surface on which computer-assisted device 120 may be wheeled, slid, and/or otherwise repositioned. In some examples, a z-axis of coordinate system $b_1$ may correspond to a vertical up direction. In some embodiments, coordinate systems $b_0$ and/or $b_1$ need not be necessarily be on the same or parallel planes, such as in the case when one or more of the computer-assisted devices 110 and/or 120 are mounted on a table, a wall, a ceiling, and/or the like.

FIG. 1 also shows an imaging device coordinate system c (e.g., for camera) that may be used to describe positions and/or orientations of objects (e.g., the distal end of instrument 124) in images captured by imaging device 114. In some examples, an origin of coordinate system c may be located at a distal end of imaging device 114. In some examples, the origin of coordinate system c may be located at a mid-point of an imaging plane associated with imaging device 114. In some examples, a z-axis of coordinate system c may be oriented in a direction of view of imaging device 114. In some examples, imaging device 114 may be a steerable imaging device and/or a flexible continuum-robot like imaging device, such that coordinate system c may be at or near a distal tip of the imaging device. In some examples, the coordinate system c may not be attached to a physical point and may be virtually coupled, rigidly or otherwise, to a reference point on the imaging device.

FIG. 1 also shows an instrument coordinate system t (e.g., for instrument 124) that may be used to describe positions and/or orientations of a constellation of points on or near instrument 124 relative to a known fixed point on instrument 124. In some examples, one or more kinematic models of computer-assisted device 120 and/or instrument 124 may be used to determine a pose of instrument coordinate system t relative to the base coordinate system $b_1$ of computer-assisted device 120. In some examples, the fixed point may correspond to a distal end of instrument 124. In some examples, the fixed point may correspond to an easily identified point feature on instrument 124, such as a fiducial, an indicia mark (including markings for indicating instrument type or source), a representative structure such as a tool tip or a clevis pin about which one or more jaws and/or links of instrument 124 may be rotated, a point at a predefined displacement from any of the above described fixed points, and/or the like. In some examples, a principal axis of coordinate system t may correspond to an alignment feature of instrument 124. An alignment feature could be a real or virtual line of symmetry, a line associated with a principal rotational and/or translational motion of instrument 124, a line integral to the shape of instrument 124, and/or the like. In some examples, the alignment feature may be an axis determined from a fiducial indicating an axis, an indicia mark indicating an axis, an axis of a shaft of instrument 124, an axis corresponding to a distinctive structure (e.g., as located between two jaws of instrument 124 and oriented with the grasping faces of the two jaws while the jaws are closed), an axis formed by a line segment connecting any of the fixed points described above, a virtual axis at a predefined origination relative to any of the above described alignment features or axes, and/or the like. In some examples, coordinate system t may not be attached to a physical point and may be virtually coupled, rigidly or otherwise, to a reference point and/or the fixed point on instrument 124.

As is further shown in the embodiments of FIG. 1, because the bases of both computer-assisted device 110 and computer-assisted device 120 may be moved and/or oriented relative to and independently of each other (e.g., they have independent kinematic chains), the geometric relationship between coordinate system $b_0$ and coordinate system $b_1$ is subject to change. In some examples, the geometric relationship between coordinate system $b_0$ and coordinate system $b_1$ may be characterized using a 6 degrees of freedom (6 DOF) registration transform $^{b_0}T_{b_1}$. As shown in Equation 1, registration transform $^{b_0}T_{b_1}$ includes a 3 degrees of freedom (3 DOF) rotation portion $^{b_0}R_{b_1}$ and a 3 DOF translation portion $^{b_0}t_{b_1}$. Rotation portion $^{b_0}R_{b_1}$ is a 3×3 matrix describing the 3-dimensional rotational difference between coordinate system $b_0$ and coordinate system $b_1$. In some examples, rotation portion $^{b_0}R_{b_1}$ describes rotation about the three axes of the coordinate system. In some examples, the three axes may correspond to x, y, and z axes; roll, pitch, and yaw axes; and/or the like. In some examples, the rotation portion may be represented using angle-axis, quaternion, and/or similar equivalent notations. Translation portion $^{b_0}t_{b_1}$ is a 3×1 vector describing the 3-dimensional displacement between coordinate system $b_0$ and coordinate system $b_1$. In some examples, registration transform $^{b_0}T_{b_1}$ may be used to determine the full transform from instrument coordinate system t to imaging device coordinate system c (e.g., $^cT_t$). In some examples, registration transform $^{b_0}T_{b_1}$ may be defined as a correction to the assumed imaging device coordinate system c (e.g., $^{c'}T_c$) where c' is the corrected coordinated system of imaging device 114 that aligns the motion of instrument 124 and motion of the one or more input controls used to control instrument 124.

$$^{b_0}T_{b_1} = \begin{bmatrix} ^{b_0}R_{b_1} & ^{b_0}t_{b_1} \\ 0 & 1 \end{bmatrix} \quad \text{Equation 1}$$

In some embodiments, when computer-assisted device 110 and computer-assisted device 120 are located on a common planar surface and have a common vertical up direction (e.g., both coordinate system $b_0$ and coordinate system $b_1$ are located on a same level reference plane and have a same vertical up axis), reference transform $^{b_0}R_{b_1}$ may be simplified to a single rotation about the vertical up axis and $^{b_0}t_{b_1}$ may be simplified to a two-dimensional (2D) lateral translation between coordinate system $b_0$ and coordinate system $b_1$. In some examples, when the bases of computer-assisted devices 110 and 120 are on parallel planes, each orthogonal to the vertical up axis and separated by a distance, reference transform $^{b_0}R_{b_1}$ may be simplified to a single rotation about the vertical up axis and $^{b_0}t_{b_1}$ may be a three-dimensional (3D) translation vector.

In some embodiments, where the 6 DOF registration transform needs to be determined, the inclination or elevation angle between the bases of computer-assisted devices 110 and 120 may be known through one or more inclinometers and/or accelerometers, thus reducing the number of DOFs of registration transform $^{b_0}t_{b_1}$ that need to be computed by other means.

Computer-assisted device 110 and computer-assisted device 120 are both coupled to a control unit 140 via respective interfaces. Each of the respective interfaces may include one or more cables, connectors, and/or buses and may further include one or more networks with one or more network switching and/or routing devices. Control unit 140 includes a processor 150 coupled to memory 160. Operation of control unit 140 is controlled by processor 150. And although control unit 140 is shown with only one processor 150, it is understood that processor 150 may be representative of one or more central processing units, multi-core processors, microprocessors, microcontrollers, digital signal processors, field programmable gate arrays (FPGAs), application specific integrated circuits (ASICs), graphics processing units (GPUs), tensor processing units (TPUs), and/or the like in control unit 140. Control unit 140 may be implemented as a stand-alone subsystem and/or as a board added to a computing device or as a virtual machine.

Memory 160 may be used to store software executed by control unit 140 and/or one or more data structures used during operation of control unit 140. Memory 160 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 160 includes a control module 170 that is responsible for controlling one or more aspects of the operation of computer-assisted device 110 and/or computer-assisted device 120 including, for example, the control of movement and/or operation of each of computer-assisted device 110, computer-assisted device 120, repositionable arm 112, repositionable arm 122, imaging device 114, and/or instrument 124; determining a registration transform between computer-assisted device 110 and computer-assisted device 120, and/or the like as is described in further detail below. And although control module 170 is characterized as a software module, control module 170 may be implemented using software, hardware, and/or a combination of hardware and software.

As discussed above and further emphasized here, FIG. 1 is merely an example which should not unduly limit the scope of the claims. One of ordinary skill in the art would recognize many variations, alternatives, and modifications. According to some embodiments, computer-assisted system 100 may further include one or more operator stations having respective one or more input controls for determining a desired motion for computer-assisted device 110, computer-assisted device 120, repositionable arm 112, repositionable arm 122, imaging device 114, and/or instrument 124. In some examples, the operator station is in the form of a console. In some examples, a single operator station may be shared between computer-assisted device 110 and computer-assisted device 120. In some examples, computer-assisted device 110 and computer-assisted device 120 may have separate operator stations. In some examples, the one or more operator stations may be coupled to computer-assisted device 100, computer-assisted device 120, and/or control unit 140 using respective interfaces. Each of the respective interfaces may include one or more cables, connectors, and/or buses and may further include one or more networks with one or more network switching and/or routing devices.

According to some embodiments, computer-assisted system 100 may include any number of computer-assisted devices with corresponding repositionable arms and/or instruments of similar or different in design from computer-assisted device 110 and/or computer-assisted device 120. In some examples, each of the computer-assisted devices may include two, three, four, or more repositionable arms and/or instruments.

According to some embodiments, each of computer-assisted devices 110 and/or 120 may have separate control units similar to control unit 140. In some examples, each of the separate control units may be coupled to each other via an interface. The interface may include one or more cables, connectors, and/or buses and may further include one or more networks with one or more network switching and/or routing devices. In some examples, the separate control units may use the interface to share and/or exchange information about their respective computer-assisted devices. In some examples, the exchanged information may include kinematic information regarding positions of one or more joints in the respective repositionable arms 112 and/or 122 and/or the respective imaging device 114 and/or 124; positions and/or orientations of imaging device 114 and/or instrument 124; and/or the like. In some examples, the exchanged information may include one or more sensor readings, mode indications, interrupts, state transitions, events, fault conditions, safety warnings, and/or the like. In some examples, the exchanged information may include one or more images captured by imaging device 114, information derived from the one or more images, calibration and/or configuration parameters specific to instrument 124 and/or imaging device 114, and/or the like.

According to some embodiments, imaging device 114 may alternatively be mounted to a fixture or be a hand-held imaging device, and not mounted to a repositionable arm of a computer-assisted device. In some examples, when imaging device 114 is not mounted to a repositionable arm of a computer-assisted device, coordinate system $b_0$ may be the same coordinate system as coordinate system c.

In computer-assisted systems with multiple separate and/or modular computer-assisted devices and repositionable arms that do not share a common known base (e.g., embodiments like those shown in FIG. 1), or for some other reason the transform relating the computer-assisted devices and/or repositionable arms are not known (e.g. one or more faulty sensors, one or more inadequate sensing systems, and/or the like), there is often a difficulty in establishing registration, or in maintaining sufficiently accurate registration, between the multiple computer-assisted devices and/or repositionable arms. This is especially important when one of the computer-assisted devices has an imaging device mounted thereto, and images captured by the imaging device are the basis for intuitive teleoperation of an instrument mounted to another repositionable arm of one of the other computer-assisted devices. In some examples, the registration may be established by determining a registration transform (e.g., registration transform $^{b_0}T_{b_1}$) between a base coordinate system (e.g., coordinate system $b_0$) of the computer-assisted device to which the imaging device is mounted, and a base coordinate system (e.g., coordinate system $b_1$) of the computer-assisted device to which the teleoperated instrument is mounted. In some embodiments, this registration difficulty also exists when a hand-held imaging device is used, and the base coordinate system for the imaging device is not tied to a base of a repositionable structure (e.g. the base coordinate system for the imaging device may be tied to the imaging device itself). In some embodiments, the registration transform may be used for collision avoidance between computer-assisted devices, overlaying user interface elements on captured images, coordinating the motions of multiple computer-assisted devices (e.g., for autonomous task sequences), and/or the like.

According to some embodiments, establishing the registration transform iteratively by monitoring motion of the instrument using the imaging device and using the monitoring to continually refine the registration transform provides several advantages over other approaches for registering computer-assisted devices. In some examples, because the refinement is iterative, the resulting registration transform need not be static and is able to update as the instrument is used, the computer-assisted devices are repositioned, and/or the like. In some examples, the iterative registration may be used to optionally avoid having to pre-exercise the instrument through a set of known movements while in the view of the imaging device in order to determine the registration transform. In some examples, one of the goals of the iterative registration is to reduce an error in the rotation portion of the registration transform (e.g., $^{b_0}R_{b_1}$) below 20 degrees and preferably below 10 degrees or even 5 degrees. In some examples, one of the goals of the iterative registration is to reduce an error in the translation portion of the registration transform (e.g., $^{b_0}t_{b_1}$) below 5 cm and in some examples below 2 cm.

Figure 2:
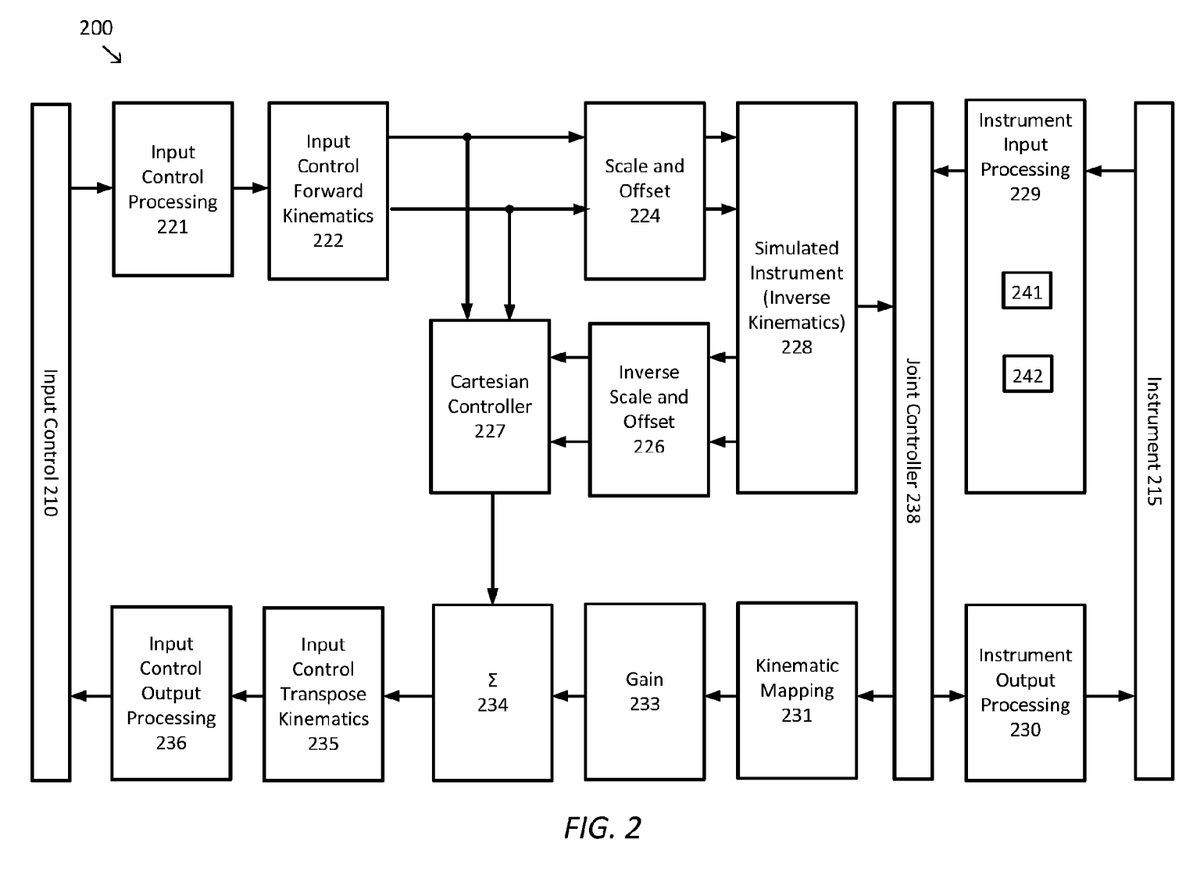
FIG. 2 is a simplified diagram of a control system according to some embodiments.

FIG. 2 is a simplified diagram of a control system 200 according to some embodiments. In some embodiments, control system 200 may be part of control module 170. In some embodiments, control system 200 may be used to control the movement of imaging device 114 and/or instrument 124 of FIG. 1. In some examples, the movement may include one or more of a position, an orientation, a pose, motion, and/or the like of imaging device 114 and/or instrument 124. In some examples, the movement may be commanded by an operator using one or more input controls. Further aspects of control system 200 are described in further detail in U.S. Patent Application Publication No. 2019/0143513, which is incorporated by reference herein.

In some embodiments, both the operator input system and the computer-assisted device used to manipulate the instrument may include a number of links connected by joints so as to facilitate control of multiple degrees-of-freedom of the instrument. As the operator moves the one or more input controls of the operator input system from a first pose to a second pose during the course of performing a procedure, sensors associated with the joints of the operator input system provide information indicating such commanded movement in the joint space of the one or more input controls. In some examples, the commanded movement includes commanded acceleration provided by sensors associated with links of the operator input system. Sensors associated with the instrument and/or the computer-assisted device provide information indicating movement of the instrument in an instrument joint space for feedback purposes.

As shown in FIG. 2, control system 200 is shown for control of an instrument 215 using an input control 210. In some examples, instrument 215 may be consistent with imaging device 114 and/or instrument 124. In some examples, control system 200 may be adapted to use multiple input controls to control instrument 215. In some examples, control system 200 may be adapted to control two or more instruments.

An input control processing unit 221 receives information of the joint positions and/or velocities of the joints in input control 210 and/or the operator input system. In some examples, the joint positions may be sampled at a control system processing rate. An input control forward kinematics processing unit 222 receives the joint positions and velocities from input control processing unit 221 and transforms them from the joint space of input control 210 to corresponding positions and velocities of a reference coordinate system associated with the operator input system. In some examples, input control forward kinematics processing unit 222 accomplishes this transformation by using a Jacobian and reference system related information. In some examples, the reference coordinate system of the operator input system may be a reference coordinate system for eyes of the operator. In some embodiments, one operating mode of control system 200 is to ensure that the motion of instrument 215 in the imaging device reference frame corresponds to the motion of input control 210 in the reference coordinate frame for the eyes of the operator.

A scale and offset processing unit 224 receives the pose, velocity, and acceleration commands from input control forward kinematics processing unit 222, scales the commanded movement according to a scale factor selected to perform a procedure, and takes into account offsets to generate a desired pose and velocity of instrument 215. The scale adjustment is useful where small movements of instrument 215 are desired relative to the larger movement of input control 210 in order to allow more precise movement of instrument 215 at a work site. The offsets determine, for example, a corresponding position and/or orientation of an instrument coordinate system (e.g., instrument coordinate system t) relative to a position and orientation of input control 210 in the reference coordinate system of the operator input system.

A simulated instrument processing unit 228 receives the desired instrument position and velocity commands from scale and offset processing unit 224 and limits the desired instrument pose, velocities, accelerations, and/or the like to assigned limits, such as to enforce correct and intuitive operation of instrument 215 by keeping instrument 215 and any associated joints within range of motion limits and/or the like. Simulated instrument processing unit 228 generates simulated instrument and computer-assisted device joint states (e.g., positions, velocities, accelerations, and/or the like). In some examples, the simulated instrument and computer-assisted device joint states are determined based on a manipulator Jacobian of instrument 215 and/or the computer-assisted device to which instrument 215 is mounted.

An inverse scale and offset processing unit 226 receives the simulated joint position and velocity commands from simulated instrument processing unit 228, and performs an inverse function (inverse to that of the scale and offset processing unit 224) on the simulated joint position and velocity commands. A Cartesian controller 227 receives the inputs to scale and offset processing unit 224 and the outputs of inverse scale and offset processing unit 226. Cartesian controller 227 then generates an error signal as a difference between the inputs to scale and offset processing unit 224 and the outputs of inverse scale and offset processing unit 226 and a Cartesian force "$F_{CART}$" from the error signal.

An input control transpose kinematics processing unit 235 receives the Cartesian force $F_{CART}$ through a summation node 234, and generates a corresponding torque in joint space using, for example, the Jacobian transpose matrix and kinematic relationships associated with the operator input system. In systems where the operator input system has actuator-driven joints for range-of-motion limits or force feedback, an input control output processing unit 236 receives the output from input control transpose kinematics processing unit 235 and generates electrical signals for controlling the actuators of the operator input system and input control 210. In some examples, the control of the actuators of the operator input system and input control 210 may be felt by the operator as haptic feedback.

As input control processing unit 221 is receiving input control 210 and operator input system joint positions from sensors, an instrument input processing unit 229 is also receiving instrument positions from sensors in instrument 215 and the computer-assisted device. In some examples, the instrument positions are received by instrument input processing unit 229 at the control system processing rate. Instrument input processing unit 229 includes an actuator-side input processing unit 241 and a load-side input processing unit 242. Actuator-side input processing using 241 receives joint measurement data (e.g., pose, velocity, acceleration, and/or the like data) from actuator-side sensors in instrument 215 and/or the computer-assisted device. Load-side input processing unit 322 receives link data (e.g., position, motion, and/or the like) of the links in instrument 215 and the computer-assisted device from load-side sensors. A joint control unit 238 receives the joint measurement data and the link data from instrument input processing unit 229 and the simulated joint commands from simulated slave processing unit 228 and generates instrument command signals for the joint actuators in instrument 215 and/or the computer-assisted device and input control feedback command signals for the joint actuators in input control 210 and/or operator input system.

The instrument command signals are generated by joint control unit 238 so as to drive joints of instrument 215 and/or the computer-assisted device until feedback errors calculated in joint control unit 238 zero out. An instrument output processing unit 230 receives the instrument command signals from joint control unit 238, converts them into appropriate electrical signals, and supplies the electrical signals to the joint actuators of instrument 215 and/or the computer-assisted device so as to drive the actuators accordingly.

The input control feedback command signals are generated by joint control unit 238 which reflect forces being exerted against instrument 215 and/or the computer-assisted device supporting instrument 215, back to the operator input system and input control 210 so that haptic feedback may be felt in some form by the operator. In some examples, joint control unit 238 may generate the input control feedback command signals based on the joint position and/or velocity tracking errors in instrument 215 and/or the computer-assisted device. A kinematic mapping unit 231 receives the input control feedback command signals from joint control unit 238 and generates the corresponding Cartesian force at the tip of instrument 215 relative to the reference coordinate system associated with the operator input system.

A gain 233 adjusts the magnitude of the Cartesian force so as to ensure system stability while providing adequate force sensation to the operator. The gain adjusted Cartesian force is then passed through summation node 234 and processed along with the Cartesian force provided by Cartesian controller 227 through input control transpose kinematics processing unit 235 and input control output processing unit 236 as previously described.

Figure 3:
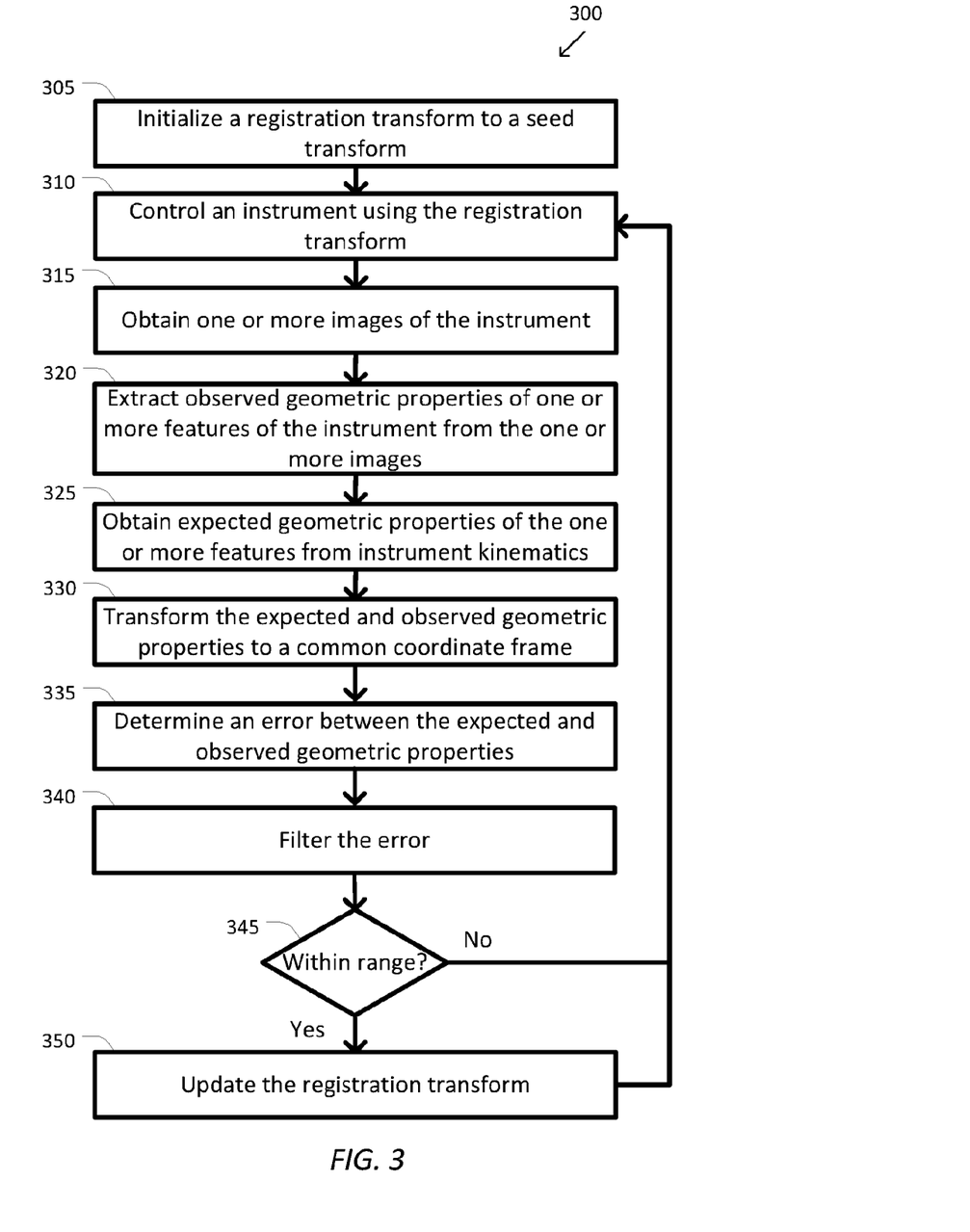
FIG. 3 is a simplified diagram of a method of registration according to some embodiments.

FIG. 3 is a simplified diagram of a method 300 of registration according to some embodiments. One or more of the processes 305-350 of method 300 may be implemented, at least in part, in the form of executable code stored on non-transitory, tangible, machine readable media that when run by one or more processors (e.g., the processor 150 in control unit 140) may cause the one or more processors to perform one or more of the processes 305-350. In some embodiments, method 300 may be performed by one or more modules, such as control module 170. In some embodiments, method 300 may be used to determine a registration transform (e.g., registration transform $^{b_0}T_{b_1}$) between a first computer-assisted device (e.g., computer-assisted device 120) having an instrument (e.g., instrument 124) mounted thereto and a second computer-assisted device (e.g., computer-assisted device 110) having an imaging device (e.g., imaging device 114) mounted thereto that is able to capture one or more images of the instrument. In some embodiments, method 300 may also be used to determine a registration transform between a computer-assisted device having an instrument mounted thereto and a handheld imaging device. In some embodiments, process 340 is optional and may be omitted. In some embodiments, method 300 may include additional processes, which are not shown. In some embodiments, one or more of the processes 305-350 may be performed, at least in part, by one or more of the units of control system 200.

At a process 305, a registration transform is initialized using a seed transform. In some examples, the seed transform is a rough estimate of the registration transform that will be iteratively refined using processes 310-350. In some examples, one or more sensors may be used to determine the seed transform. In some examples, the one or more sensors may include an inertial measurement unit (IMU) for the imaging device, the instrument, or both the imaging device and the instrument. In some examples, the one or more sensors may further include one or more gravity sensors (e.g., accelerometers and/or inclinometers) and/or one or more magnetometers. In some examples, the one or more sensors may be associated with one or more tracking systems (e.g., electromagnetic and/or optical trackers).

In some embodiments, the seed transform may be determined by tracking one or more known movements of the imaging device and/or the instrument. In some examples, the one or more known movements may overlap the motions of the imaging device and/or the instrument being performed for other purposes. In some examples, the one or more known movements may be commanded by an operator using an operator station. In some examples, the one or more known movements may include one or more small motions that begin automatically and/or in response to an initiation triggered by the operator. In some examples, an image (e.g., a static image) captured by the imaging device just before the one or more small motions are begun may be displayed to the operator while the one or more small motions occur so that the one or more small motions are not visible to the unaided eye of the operator. In some examples images captured live by the imaging device may be displayed to the operator after the one or more small motions are completed.

In some embodiments, the one or more known movements may be one or more motions, in known directions of the imaging device and/or instrument coordinate system, that are superimposed on the movements of the imaging device and/or the instrument that are commanded by the operator. In some examples, the one or more small motions may be consistent with the technique of Eulerian Amplification. In some examples, the one or more small motions may include motions that occur at a frequency that is above typical movements commanded by the operator during teleoperation (e.g., motions with a frequency greater than 10 Hz). In some examples, the one or more small motions may be separated, during data processing, from the movements commanded by the operator using high-pass filtering.

In some embodiments, the one or more known movements and/or the one or more small motions may be continued until a sufficient number of images showing the relative position and/or orientation of the instrument relative to the imaging device are captured, such that when they are combined with the forward and/or inverse kinematic models of the first and second computer-assisted devices are able to provide sufficient data for determining one or more estimates for each relevant unknown of the registration transform (e.g., unknowns from the rotation portion and/or the translation portion of the seed transform). In some examples, multiple estimates for the unknowns may be aggregated by averaging, least-squares estimation, and/or the like. In some examples, when the computer-assisted devices to which the instrument and the imaging device are respectively mounted are located on a common planar surface and have a common vertical up direction a common vertical up axis, at least two images are captured. In some examples, when the computer-assisted devices to which the instrument and the imaging device are respectively mounted are not located on a common planar surface or do not have a common vertical up axis, at least three images are captured. In some examples, the duration of the one or more known movements and/or the one or more small motions and the number of images sampled is determined based on a trade-off between an accuracy of the seed transform, a time to complete process 305, and/or a number of features (e.g., points, line segments, axes, directed vectors, free vectors, and the like) observed in the image.

In some embodiments, the translation portion of the seed transform may be determined from one or more images of the instrument captured by the imaging device. In some examples, when a location of a point feature on the instrument (e.g., a fiducial, an indicia mark, a representative structure such as a tool tip or a clevis pin, and/or the like) may be determined relative to an imaging device coordinate system (e.g., coordinate system c), the relative location and the forward and/or inverse kinematic models of the first and second computer-assisted devices may be used to determine the translation portion (e.g., translation portion $^{b_0}t_{b_1}$) of the seed transform. In some examples, when the imaging device is able to capture partial or complete 3D information (e.g., it is a stereoscopic endoscope, provides depth information in addition to images, and/or the like) the relative location of the point feature may be determined from the imaging data directly. In some examples, when the imaging device is only able to capture 2D information, multiple images with the imaging device moving, the instrument moving, and/or both the imaging device and the instrument moving, between the images may be used to solve for the relative location of the point feature. In some examples, the translation portion of the seed transform may use multiple images and/or sets of images to more accurately determine the relative location of the point feature. In some examples, the relative location estimates from each of the multiple images, or from sets of images, may be aggregated together, such as by using averaging, least squares estimation, and/or the like. In some examples, relative locations determined for multiple point features and/or a feature set may be aggregated to determine the translation portion of the seed transform.

At a process 310, the instrument is controlled using the registration transform. In some embodiments, the registration transform may be used to help more intuitively map movements of the one or more input controls on the operator station to movements of the instrument (e.g., so that movement of the one or more input controls relative to the eye coordinate system of the operator station more closely matches the corresponding movement of the instrument relative to the imaging device). In some examples, movements of the one or more input controls in the eye coordinate system of the operator station are converted to corresponding movements of the instrument relative to the imaging device. The registration transform is used to map the corresponding movements of the instrument relative to the imaging device $^{c}v_{kinematics}$ to corresponding movements of the instrument relative to the base coordinate system of the computer-assisted device to which the instrument is mounted $^{t}v_{kinematics}$. In some examples, this mapping may be determined using Equation 2, where $^{b_1}T_t$ is the forward kinematic transform from the instrument to the base coordinate system of computer-assisted device to which the instrument is mounted, $^{b_0}T_{b_1}$ is the registration transform, and $^{b_0}T_c$ is the forward kinematic transform from the imaging device to the base coordinate system of the computer-assisted device to which the imaging device is mounted.

$$^{t}v_{kinematics} = (^{b_1}T_t)^{-1}(^{b_0}T_{b_1})^{-1}(^{b_0}T_c)^{c}v_{kinematics} \quad \text{Equation 2}$$

In some examples, the movements of the one or more input controls in the eye coordinate system of the operator station (e.g., the output of scale and offset processing unit 224), the corresponding movements of the instrument relative to the imaging device $^{c}v_{kinematics}$, and/or the corresponding movements of the instrument relative to the base coordinate system of the computer-assisted device to which the instrument is mounted $^{t}v_{kinematics}$ may be expressed as 3 DOF position, 3 DOF orientation, 3 DOF translational velocity, 3 DOF angular velocity, and/or a subset thereof, of a reference coordinate system of interest. These commanded motion attributes at the operator station are termed as "desired" or "expected", and are associated with a reference coordinate system of interest of the operator station. In some examples, the reference coordinate system of interest may be associated with the one or more input controls. In some examples, the same motion attributes as measured on the instrument using images from the imaging device are termed "observed."

At a process 315, one or more images of the instrument are obtained. In some examples, the one or more images may be captured by the imaging device. In some examples, the data may include left and right 3D images from a stereoscopic imaging device, 3D images from multiple imaging devices setup to capture images from different perspectives, and/or 3D depth or intensity maps from the imaging device.

At a process 320, observed geometric properties of one or more features of the instrument are extracted from the one or more images. In some examples, the one or more observed geometric properties may correspond to one or more positions, one or more velocities, one or more rotational velocities, and/or the like. In some examples, each of the observed geometric properties may be modeled as a point, a transmissible vector, a free vector, a bound vector, and/or suitable combinations of any of these. In some examples, the one or more features of the instrument may include one or more primary features and/or one or more secondary features.

In some examples, the primary features are determined from the one or more images using computer vision algorithms to detect known fiducials on the instrument, detectable features of the instrument, and/or the like. In some examples, a machine learning and/or artificial intelligence (AI) module may be used to observe primary features of interest on the instrument. In some examples, the machine learning and/or AI module may consist of a deep convolutional neural network that is trained to detect particular features on the instrument such as an identifiable point feature on the instrument, such as a fiducial, an indicia mark (including markings for indicating instrument type or source), a representative structure such as a tool tip or a clevis pin about which one or more jaws and/or links of the instrument may be rotated, and/or the like. In some examples, the one or more primary features may correspond to an alignment feature of the instrument, such as a real or virtual line of symmetry, a line associated with a principal rotational and/or translational motion of the instrument, a line integral to the shape of the instrument, and/or the like. In some examples, the alignment feature may be an axis determined from a fiducial indicating an axis, an indicia mark indicating an axis, an axis of a shaft of the instrument, an axis corresponding to a distinctive structure (e.g., as located between two jaws of the instrument and oriented with the grasping faces of the two jaws while the jaws are closed), an axis formed by a line segment connecting any of the point features described above, and/or the like.

In some examples, the one or more secondary features may correspond to one or more points of interest on the kinematic chain of the computer-assisted device holding the instrument such as the remote center of motion. In some examples, the one or more secondary features may correspond to a point and/or an axis with a pre-defined linear and/or angular displacement from any of the one or more primary features. In some examples, the secondary features may be determined using one or more estimators which use the kinematics information of the computer-assisted devices to which the imaging device and/or the instrument are mounted and/or the one or more primary features detected in the one or more images. In some examples, each of the estimators may be a Kalman filter, a state-observer, and/or the like. In some examples, the one or more secondary features may be derived from a 3D model of a part of the instrument that is at least partially visible in the one or more images. In some examples, the 3D model of the part may be registered to the observed part using model-matching and/or the like. In some examples, the one or more secondary features may be derived by a data fusion process that combines information from the one or more primary features and one or more other sensors such as one or more accelerometers, inclinometers, IMUs, and/or the like. In some examples, a combination or subset of the one or more primary features and/or the one or more secondary features may be used depending on occlusion of part of the instrument in the field of view of the imaging device; an accuracy of observing and/or estimating a feature, a lighting condition, a color variations; a change of instrument during a procedure; an absence of an instrument in the field of view of the imaging device, and/or the like. Additional examples of process 320 are described in further detail with respect to FIG. 4A.

At a process 325, expected geometric properties of the one or more features are extracted from instrument kinematics. In some examples, the expected geometric properties of the one or more features correspond to the same observed geometric properties of the same one or more features whose observed geometric properties are extracted from the one or more images during process 320. In some examples, the expected geometric properties of the one or more features are time synchronous to the same observed geometric properties of the same one or more features so that the expected and observed geometric properties are based on information about the one or more features obtained at approximately the same period in time. In some examples, the instrument kinematics correspond to information about the kinematic chain of the instrument and the computer-assisted device to which the instrument is mounted. In some examples, the information regarding the kinematic chain of the instrument may be determined based on one or more joint positions and/or orientations of the computer-assisted device to which the instrument is mounted, one or more joint positions and/or orientations of a repositionable arm to which the instrument is mounted, one or more joint positions and/or orientations of the instrument, and one or more corresponding kinematic models. Additional examples of process 325 are described in further detail with respect to FIG. 4B.

At a process 330, the expected and observed geometric features are transformed to a common coordinate system using the registration transform. The common coordinate system allows for direct comparison between (i) a first estimate of geometric properties of the one or more features of the instrument determined based on the one or more images during process 320 and (ii) a second estimate of the same or related geometric properties of the one or more features of the instrument determined based on instrument kinematics determined during process 325, the information about the kinematic chain of the computer-assisted device to which the instrument is mounted, and information about a kinematic chain of the computer-assisted device to which the imaging device is mounted. In some examples, the common coordinate system is a coordinate system of the instrument (e.g., coordinate system t), a coordinate system of the imaging device (e.g., coordinate system c), a base coordinate system of the computer-assisted device to which the instrument is mounted (e.g., coordinate system $b_1$), and/or a base coordinate system of the computer-assisted device to which the imagine device is mounted (e.g., coordinate system $b_0$). In some examples, the common coordinate system may be chosen to be any other reference coordinate system different from coordinate systems $b_0$, $b_1$, t, or c. In some examples the reference coordinate system may be chosen based on a procedure being performed, a type of the instrument, a type of the imaging device, operator preference, and/or the like as long as suitable kinematic transforms may be determined to transform both the expected and observed geometric properties to the reference coordinate system.

In some examples, when the common coordinate system is the coordinate system of the imaging device, the observed geometric properties of the one or more features of the instrument determined during process 320 are already available in the coordinate system of the imaging device, and the expected geometric properties of the one or more features of the instrument in the coordinate system of the instrument $^t v_{kinematics}$ may be transformed to expected geometric properties in the coordinate system of the imaging device $^c v_{kinematics}$ using Equation 3, where $^{b_0}T_t$ is the forward kinematic transform from the instrument to the base coordinate system of computer-assisted device to which the instrument is mounted, $^{b_0}T_{b_1}$ is the registration transform, and $^{b_0}T_c$ is the forward kinematic transform from the imaging device to the base coordinate system of the computer-assisted device to which the imaging device is mounted.

$$^c v_{kinematics} = (^{b_0}T_c)^{-1}(^{b_0}T_{b_1})(^{b_1}T_t)^t v_{kinematics} \quad \text{Equation 3}$$

In some examples, when the common coordinate system is the coordinate system of the instrument, the expected geometric properties of the one or more features of the instrument determined during process 325 are already available in the coordinate system of the instrument, and the observed geometric properties of the one or more features of the instrument determined during process 320 may be transformed to the coordinate system of the instrument using the approach of Equation 2.

Similar approaches may be used for other common coordinate systems including coordinate system $b_0$, coordinate system $b_1$, and/or any of the reference coordinate systems described above. In some examples, variations of Equations 2 and 3 may be used with the reference transform and suitable forward and/or inverse kinematic transforms of the instrument, the imaging device, and/or the forward and/or inverse kinematic transforms between the common coordinate system and the base coordinate system of the appropriate computer-assisted device.

In some examples, the information regarding the kinematic chain of the imaging device may be determined based on one or more joint positions and/or orientations of the computer-assisted device to which the imaging device is mounted, one or more joint positions and/or orientations of a repositionable arm to which the imaging device is mounted, one or more joint positions and/or orientations of the imaging device, and one or more corresponding kinematic models. In some examples, the information regarding the kinematic chain of the imaging device may be supplemented using system calibration and/or configuration parameters such as imaging device calibration, imaging device settings, system settings, and/or the like.

In some examples, when the imaging device is hand-held, a position and/or an orientation of the imaging device, may be determined from information obtained from one or more sensors, one or more tracking units, one or more IMUs, and/or the like.

At a process 335, an error between the expected and observed geometric properties is determined in the common coordinate system. In some examples, the error may describe an error in the registration transform. In some examples, the error may additionally and/or alternatively be determined from a difference between changes in the expected and observed geometric properties. In some examples, the registration transform error $\Delta T$ may be computed by solving an optimization problem that minimizes the difference between the expected and observed geometric features as shown in Equation 4.

$$\text{minimize}(^{b_0}T_c {}^c v_{vision} - \Delta T {}^{b_0}T_{b_1} {}^{b_1}T_t {}^t v_{kinematics}) \quad \text{Equation 4}$$

In some examples, the optimization problem may be solved by a weighted least squares method when the expected and observed geometric properties correspond to point features, alignment features, and/or the like of the one or more features that can be matched using the registration transform error $\Delta T$. In some examples, when there is no correspondence between the expected and observed geometric properties, the optimization problem may be solved by a method such as an iterative closest point algorithm and/or the like. Additional examples of the determination of the error are described in further detail below with respect to FIGS. 4C and/or 5.

At an optional process 340, the error is filtered. In some examples, error determined during process 335 is passed through a frequency-domain filter to smooth the transition between previous and current registration transform updates. In some examples, separate filters may be used for the rotation and the translation portions of the error depending on a baseline noise level in the determinations of the expected and/or observed geometric properties. In some examples, the filters used to process different degrees of freedom within the translation or rotation portions may also be different.

At a process 345, it is determined whether the error or filtered error magnitude is within a suitable range for use in updating the registration transform. In some examples, the translation and/or rotation portion of the error or filtered error may be compared to a corresponding configurable upper limit to determine whether the error or filtered error may provide for a safe and/or allowable update to the registration transform. In some examples, the corresponding configurable upper limit may be a constant depending on a maximum allowable difference in the registration transform between successive iterations of method 300. In some examples, the corresponding configurable upper limit may be variable depending on the maximum allowable instantaneous difference in the registration transform between successive iterations of method 300 in a particular configuration of the computer-assisted devices, the instrument, and/or the imaging device. In some examples, the corresponding configurable upper limit may be determined based on one or more of a procedure being performed, a type of the instrument, a type of the imaging device, a type of either of the computer-assisted devices, operator preference, and/or the like.

In some examples, the translation and/or rotation portion of the error or filtered error magnitude may be compared to a corresponding configurable lower limit to determine whether the error or filtered error indicates that a registration transform update should be performed. In some examples, the corresponding configurable lower limit may be set depending on a maximum error in alignment that is perceivable by the operator, a maximum error in alignment that can measurably decrease the efficacy of the operator during a procedure, and/or the like. In some examples, the corresponding configurable lower limit may be 5 degrees for the rotation portion of the error or filtered error and/or 2 cm for the translation portion of the error or filtered error. In some examples, the corresponding configurable lower limit may be determined based on one or more of a procedure being performed, a type of the instrument, a type of the imaging device, a type of either of the computer-assisted devices, operator preference, and/or the like.

When it is determined that the error or filtered error magnitude is within the suitable range (e.g., the error is larger than the configurable lower limit and/or smaller than the configurable upper limit), the registration transform is updated using a process 350. When it is determined that the error or filtered error magnitude is not within the suitable range, method 300 repeats by returning to process 310 without updating the registration transform. In some embodiments, in addition to checking the range of error magnitudes, the rate of convergence of registration error is also used as a check to determine if the registration transform is updated using a process 350. As modeled, the registration error should monotonically decrease with time as successive corrections are made. In some examples, the registration error trend may be computed to ensure that the error magnitude is, on an average, progressively converging toward a lower limit.

At process 350, the registration transform is updated. In some examples, the error or the filtered error are used to determine a change in the rotation portion of the registration transform and/or a change in the translation portion of the registration transform.

In some examples, the change in the rotation portion of the registration transform is determined from the angular error determined during process 335 and as optionally filtered by process 340. In some examples, the change in the rotation portion of the registration transform may be a 3×3 rotation matrix ($\Delta R$) describing errors in the rotation angles of the rotation portion of the registration transform. In some examples, the rotation portion of the registration transform is updated by composing the change in the rotation portion of the registration transform determined from the current iteration (i) of method 300 (e.g., rotation matrix $\Delta R(i)$) with the current rotation portion of the registration transform at the current iteration $^{b_0}R_{b_1}$ (i) to determine the updated registration portion of the registration transform $^{b_0}R_{b_1}$ (i+1) for use in the next iteration (i+1) as shown in Equation 5.

$$^{b_0}R_{b_1}(i+1) = \Delta R(i)\, ^{b_0}R_{b_1}(i) \qquad \text{Equation 5}$$

In some examples, the translation portion of the registration transform at the next iteration $^{b_0}t_{b_1}$ (i+1) of method 300 is updated by composing the change in the rotation portion of the registration transform determined from the current iteration (i) of method 300 (e.g., rotation matrix $\Delta R(i)$ with the translation portion of the registration transform for the current iteration $^{b_0}t_{b_1}$ (i) of method 300 and add the result to the translation portion of the error or filtered error (e.g., translation vector $\Delta t(i)$), the rotation portion of the error or filtered error as shown in Equation 6.

$$^{b_0}t_{b_1}(i+1) = \Delta t(i) + \Delta R(i)\, ^{b_0}t_{b_1}(i) \qquad \text{Equation 6}$$

In some examples, the registration transform is updated by combining the rotation portion of the registration $^{b_0}R_{b_1}$ (i+1) for the next iteration of method 300 with the translation portion of the registration transform $^{b_0}t_{b_1}$ (i+1) for the next iteration of method 300 using Equation 1. After the registration transform is updated by process 350, method 300 repeats by returning to process 310.

In some embodiments, processes 310-350 of method 300, may be executed within a closed-loop real-time control system in the control unit 140, such that a registration transform update is available at every sample of the control system. As a result, as the instrument continues to be controlled, the updating of the registration transform may be repeated by repeating processes 310-350 during every loop of the control system. In some examples, sensor input into the control system and registration transform output from the control system may be at different sampling rates in comparison to the execution rate of the control system itself; however such peripheral communications are generally synchronized with the control system such that the expected and observed geometric properties of the one or more features of the instrument are time-synchronous.

Figure 4A:
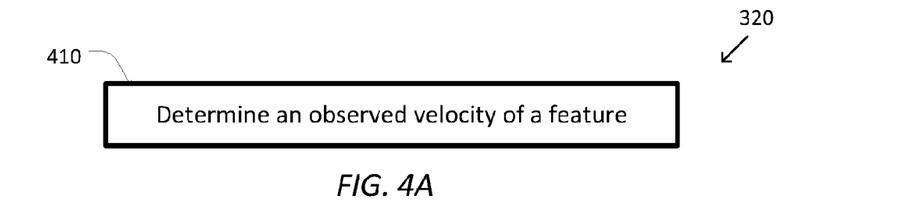
FIGS. 4A-4C are simplified diagrams of several processes of the method of FIG. 3 according to some embodiments.
Figure 4B:
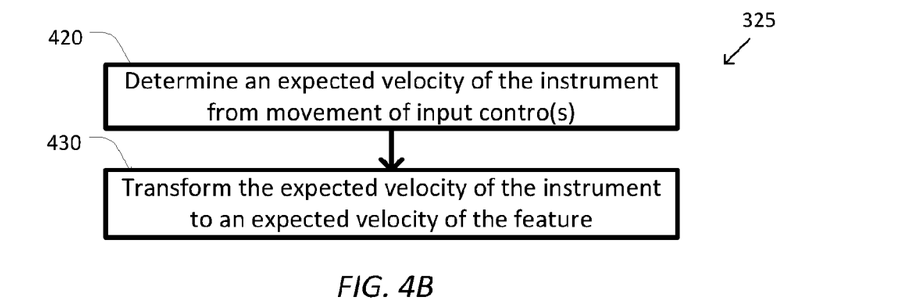
Figure 4C:
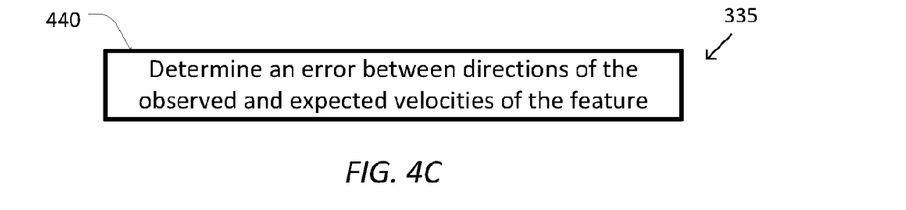
Figure 5:
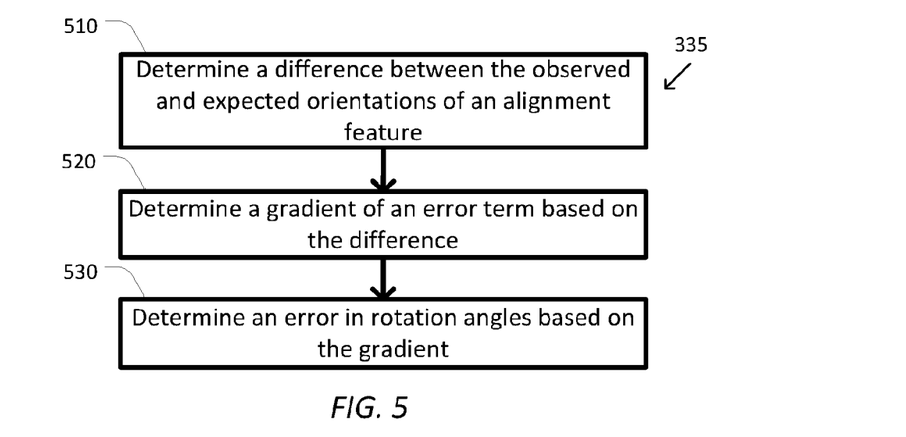
FIG. 5 is a simplified diagram of a process of the method of FIG. 3 according to additional embodiments.

FIGS. 4A-4C are simplified diagrams of several processes of method 300 according to some embodiments. More specifically, the embodiments of FIGS. 4A-4C correspond to implementations in which a 6 DOF pose and velocity of the one or more input controls is known in the eye coordinate system of the operator station, such that the movements of the one or more input controls with respect to the eye coordinate system of the operator station may be used to determine corresponding expected movements of the instrument in the imaging device coordinate system. In some examples, expected movements of the instrument in the imaging device coordinate system may correspond to an expected 3 DOF position, an expected 3 DOF orientation, an expected 3 DOF translational velocity, and/or an expected 3 DOF angular velocity of the instrument, or a subset thereof. FIG. 4A shows process 410 for implementing process 320 of method 300 under these implementations, FIG. 4B shows processes 420 and 430 for implementing process 325 of method 300 under these implementations, and FIG. 4C shows process 440 for implementing process 335 of method 300 under these implementations.

Referring to FIG. 4A, at a process 410 an observed velocity of a feature of the instrument is determined based on images obtained from the imaging device. In some examples, successive images over time are obtained from the imaging device. In some examples, the successive images may correspond to an image obtained during process 315 of the current iteration through processes 310-350 and an image obtained during process 315 of a previous iteration through processes 310-350.

In some examples, the observed velocity corresponds to a change in position of a point feature on the instrument. In some examples, the point feature may correspond to a primary point feature, such as a fiducial, an indicia mark, a representative structure such as tool tip or a clevis pin about which jaws of the instrument may be rotated, and/or the like visible in the images. In some examples, the point feature may correspond to a secondary point feature determined from one or more primary features. In some examples, the observed velocity may be modeled as a 3D velocity using, for example, $\Delta x$, $\Delta y$, and $\Delta z$ values.

In some examples, the velocity corresponds to a change in orientation of an alignment feature of the instrument. In some examples, the alignment feature may be a primary alignment feature such as an axis determined from a fiducial indicating an axis, an indicia mark indicating an axis, an axis corresponding to a distinctive structure (e.g., as located between two jaws of the instrument and oriented with the grasping faces of the two jaws while the jaws are closed), and/or the like. In some examples, the alignment feature may be a secondary alignment feature determined from one or more primary features. In some examples, the change in the orientation of the alignment feature may be modeled as rotational changes about three independent axes. In some examples, the three independent axes may be roll, pitch, and yaw; x, y, and z; and/or the like. In some examples, the change in the orientation of the alignment feature may be modeled using quaternions.

In some examples, the observed velocity may be modeled as a 3D translational velocity of a point cloud consisting of a feature set. In some examples, the observed velocity may be modeled as the 6 DOF spatial velocity, including a 3 DOF translational velocity and a 3 DOF angular velocity, of a reference coordinate system on the instrument. In some examples, the reference coordinate system may be attached to a wrist center of the instrument. In some examples, the reference coordinate system may be attached to a link distal to a distal-most joint through which an orientation of a distal portion of the instrument may be articulated. In some examples, the reference coordinate system may be located anywhere on or near the instrument and may be selected based on a type of the instrument, a procedure being performed, operator preference, and/or the like. In some examples, when the observed velocity is a set of observed velocities for a feature set, these multiple observed velocities may be mapped to one point feature using a linear or non-linear weighted mean and/or other aggregation.

Referring to FIG. 4B, at a process 420, an expected velocity of the instrument is determined from movement of the one or more input controls. In some examples, the expected velocity may be time-synchronous with the observed velocity determined during process 410. In some examples, the expected velocity of the instrument is determined from a velocity of the one or more input controls, and/or from a change in position and/or orientation of the one or more input controls between successive iterations through processes 310-350. In some examples, the velocity of the one or more input controls may be mapped to the velocity of the instrument using the known transform between the one or more input controls in the eye coordinate system of the operator station. In some examples, the mapping may include a pre-determined motion scaling between the input controls and the instrument, such as may be implemented by scale and offset unit 224. In some examples, the mapping may include signal processing such as filtering, offsetting, and/or the like.

At an optional process 430, the expected velocity of the instrument is transformed to the expected velocity of the feature. When the feature whose observed velocity was determined during process 410 is not the same feature of the instrument that is being controlled by the one or input controls, the expected velocity of the instrument as determined from the movement of the one or more input controls during process 420 is transformed to the expected velocity of the feature. In some examples, one or more kinematic and/or geometric models of the instrument may be used to transform the expected velocity of the instrument to the expected velocity of the feature.

Referring to FIG. 4C, at a process 440, an error between the directions of the observed and expected velocities of the feature is determined. In some examples, the error between the directions of the observed and expected velocities may correspond to an angular difference or rotation between the observed and expected changes in position (e.g., translational velocities) of a point feature and/or the angular difference between the observed and expected change in orientations of an alignment feature. In some examples, the error between the observed and expected velocities of the one or more features is determined using an approach described with respect to process 335. In some examples, during the determination of the error between the observed and expected velocities, one or more of the following errors may be either substantially smaller than the requirement for the registration transform error, or may be well-characterized and compensated for: the control system tracking error for manipulator inverse kinematics, calibration errors in manipulator kinematics, and/or the control system tracking error for the input control and instrument teleoperation loop (e.g., as described with respect to control system 200).

FIG. 5 is a simplified diagram of process 335 of method 300 according to additional embodiments. More specifically, the embodiments of FIG. 5 correspond to implementations in which the transform between the one or more input controls and the instrument is not known in the eye coordinate system of the operator station and/or is not used. FIG. 5 shows processes 510-530 for implementing process 335 of method 300 under these implementations.

At a process 510, a difference between the observed and expected orientations of an alignment feature is determined.

In some examples, the difference may correspond to an angular difference between the observed and expected orientations of the alignment feature. In some examples, the observed and expected orientations of the alignment feature may be time-synchronous. In some examples, the alignment feature may be an primary alignment feature such as an axis determined from a fiducial indicating an axis, an indicia mark indicating an axis, an axis corresponding to a distinctive structure (e.g., as located between two jaws of the instrument and oriented with the grasping faces of the two jaws while the jaws are closed), and/or the like. In some examples, the alignment feature may be a secondary alignment feature determined from one or more primary features. In some examples, when the computer-assisted device to which the imaging device is mounted and the computer-assisted device to which the instrument is mounted are located on a common planar surface and have a common vertical up axis, the difference may correspond to an angular difference about the common vertical up axis. In some examples, when the first and second computer-assisted devices are not located on a common planar surface or do not have a common vertical up axis, the difference may correspond to an angular difference about the three axes of the common coordinate system. In some examples, the change in the orientation of the alignment feature may be modeled as rotational changes about three independent axes. In some examples, the three independent axes may be roll, pitch, and yaw; x, y, and z; and/or the like. In some examples, the change in the orientation of the alignment feature may be modeled using quaternions. In some examples, the difference between the observed and actual orientations of alignment axis may be determined using an approach described with respect to process 335.

At a process 520, a gradient of an error term based on the difference is determined. In some examples, the error term may be equal to a vector norm of the difference. In some examples, the error term may be equal to the difference. In some examples, the gradient is computed based on the difference determined during process 410 for the current iteration of processes 310-350 and the difference determined during process 410 for a previous iteration of processes 310-350.

At a process 530, an error in the rotation angles is determined based on the gradient. In some examples, Equation 7 may be used to determine the error in the rotation angles do, where k is one or more tuned parameters. In some examples, k is a scalar parameter when the first and second computer-assisted devices are located on a common planar surface and have a common vertical up axis. In some examples, k is a 3×3 parameter matrix when the first and second computer-assisted devices are not located on a common planar surface and have a common vertical up direction axis. In some examples, k may be tuned based on one or more of operator preference, a type of the instrument and/or the imaging device, a type of the first and/or second computer-assisted devices, and/or the like.

$$d\theta = -k * \text{gradient}(\text{error term}) \quad \text{Equation 7}$$

As discussed above and further emphasized here, FIGS. 3, 4A-4C, and/or 5 are merely examples which should not unduly limit the scope of the claims. One of ordinary skill in the art would recognize many variations, alternatives, and modifications. According to some embodiments, process 305 may be periodically repeated. In some examples, a new seed transform may be determined by repeating process 305, such as when a base of one or more of the first or second computer-assisted devices is moved. In some examples, when the coordinate system of the instrument (e.g., coordinate system t) can be determined from the captured images, the entire registration transform may be determined from the determination of the coordinate system of the instrument. In some examples, the coordinate system of the instrument may be determined from a point on the instrument (e.g., a point feature) and two or more axes that can be used to span the 3D image space. In some examples, one or more fiducials, one or more indicia, and/or or more structures on the instrument may be used to determine the point and the two or more axes.

According to some embodiments, the registration transform may be used to map keep-out regions of the workspace onto the images of the workspace captured by the imaging device and displayed to the operator. In some examples, the keep-out regions correspond to regions within the workspace where the instrument is not allowed to or is urged away from entering. In some examples, the keep-out regions may be indicated by one or more visual cues (e.g., barriers, shaped or cross-hatched regions, and/or the like) superimposed on the captured images. In some examples, the keep-out regions may correspond to haptic walls and/or haptic-response regions that are used to provide haptic feedback to the operator using the one or more input controls; for example, the haptic feedback may resist input control movement past a haptic wall and/or entry into a haptic region. In some examples, the keep-out regions are measured using a depth or intensity map generated by the imaging device. In some examples, the keep-out regions are detected by a trained machine learning module using depth, intensity, and/or color data sets, among other variables such as lighting conditions, to detect the keep-out regions. In some medical examples, the keep-out regions correspond to safety-critical anatomical structures such as tissue, bone, nerves, blood vessels, and/or the like.

According to some embodiments, a magnitude of the error determined during process 335 and/or process 340 may be used to control the speed at which the instrument is teleoperated using the one or more input controls during process 310. In some examples, the speed of the teleoperation is inversely scaled according to a magnitude of the error so that error with a larger magnitude results in a lower maximum speed of the teleoperation and so that error with a smaller magnitude results in a higher allowed speed of the teleoperation. In some examples, the speed of the teleoperation may be adjusted by changing a scaling factor between an amount of movement of the one or more input controls and an amount of corresponding movement of the instrument. In some examples, the speed of the teleoperation may be adjusted by setting an upper speed limit on the rate at which the instrument may be moved. In some examples, the magnitude of the error may be used to set a gain on the amount of haptic feedback applied to the one or more input controls, with a higher magnitude of error resulting in a greater amount of haptic feedback. In some examples, the speed at which the instrument is teleoperated may be scaled only when the teleoperation moves the instrument in a direction that increases the magnitude of the error.

According to some embodiments, the registration transform may be initialized during process 305 using techniques other than a seed transform. In some examples, any other registration technique may be used to initialize the registration transform such that processes 310-350 may be used to continually update the registration transform determined using that other registration technique. In some examples, the other registration technique may include one or more of touch-based registration where the instrument is teleoperated to one or more known positions and/or orientations, registration using one or more registration devices (e.g., a shape sensor, an articulated linkage, and/or the like), and/or the like.

According to some embodiments, method 300 may be adapted to situations where there are different configurations of computer-assisted devices, repositionable arms, and/or instruments. In some examples, when additional computer-assisted devices having different base coordinate systems are present, method 300 may be applied separately for each of the additional computer-assisted devices to determine and iteratively update a respective registration transform for each of the additional computer-assisted devices. In some examples, when the first computer-assisted device has additional instruments (both with or without separate corresponding repositionable arms), each of the instruments may be used in the determination of the seed transform and/or the registration transform for the first computer-assisted device. In some examples, a contribution from each of the instruments (e.g., a translation portion value, a seed transform, and/or an error used to determine the change in the rotation registration transform) may be determined separately and then aggregated together (e.g., by averaging, least squares estimation, and/or the like). In some examples, processes 310-340 may be performed separately for each of the instruments, with each of the instruments contributing to an update of the registration transform in turn, before cycling again through each of the instruments. In some examples, the contribution to each of the instruments to the update to the registration transform may be weighted based on a magnitude of the error determined during process 335 and/or process 340 for the respective instrument. In some examples, the weighting of the update to the registration transform by each instrument may be proportional to the magnitude of the error for that instrument. In some examples, the weights may be normalized relative to a total of the magnitudes of the errors.

According to some embodiments, when multiple instruments are visible in the captured images, the movements of the instruments determined from the captured images may be correlated with the movements of the one or more input controls used to control the instruments to determine which instrument is associated with each of the one or more input controls. In some examples, the association may be assisted by the operator by manipulating the instruments one at a time, manually selecting the associations, and/or the like.

Some examples of control units, such as control unit 140 may include non-transitory, tangible, machine readable media that include executable code that when run by one or more processors (e.g., processor 150) may cause the one or more processors to perform the processes of method 300 and/or the processes of FIGS. 3A, 3B, 4A, and/or 4B. Some common forms of machine readable media that may include the processes of method 300 and/or the processes of FIGS. 3A, 3B, 4A, and/or 4B are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and, in a manner, consistent with the scope of the embodiments disclosed herein.

What is claimed is:

1. A computer-assisted system comprising:
a control unit coupled to a repositionable arm of a computer-assisted device;
wherein the control unit is configured to:
receive, from an imaging device, successive images of an instrument mounted to the repositionable arm;
determine an observed velocity of a feature of the instrument based on the successive images;
determine an expected velocity of the feature of the instrument based on kinematics of the repositionable arm;
transform the observed velocity, the expected velocity, or both the observed and expected velocities to a common coordinate system using a registration transform;
determine an error between a direction of the observed velocity and a direction of the expected velocity in the common coordinate system; and
update the registration transform based on the determined error.

2. The computer-assisted system of claim 1, wherein:
the instrument is a medical instrument and the imaging device is an endoscope, and
wherein the registration transform is between a base coordinate system of the computer-assisted device and a coordinate system associated with the imaging device.

3. The computer-assisted system of claim 1, wherein the control unit is further configured to control the instrument using the registration transform.

4. The computer-assisted system of claim 1, wherein:
the feature is a point feature of the instrument; and
the observed velocity of the feature comprises a change in position of the point feature in the successive images.

5. The computer-assisted system of claim 1, wherein:
the feature is an alignment feature of the instrument; and
the observed velocity of the feature comprises a change in orientation of the alignment feature in the successive images.

6. The computer-assisted system of claim 1, wherein:
the feature is a feature set comprising a plurality of features; and
the observed velocity of the feature set is an aggregation of observed velocities for the features in the feature set.

7. The computer-assisted system of claim 1, wherein the feature is a primary feature observable in the successive images, or is a secondary feature determined from one or more primary features observable in the successive images.

8. The computer-assisted system of claim 1, wherein:
the feature corresponds to a fiducial of the instrument, an indicia mark of the instrument, or a structure of the instrument; or
the feature is a virtual feature having a predefined displacement or predefined rotation relative to the instrument.

9. The computer-assisted system of claim 1, wherein to determine the expected velocity of the instrument, the control unit is configured to:
determine an expected velocity of the instrument from movement of one or more input controls used to manipulate the instrument; and transform the expected velocity of the instrument to the expected velocity of the feature.

10. The computer-assisted system of claim 1, wherein to update the registration transform, the control unit is configured to update a rotation portion of the registration transform based on the error while not updating a translation portion of the registration transform based on the error.

11. The computer-assisted system of claim 1, wherein the control unit is further configured to initialize the registration transform from a seed transform or another registration method.

12. The computer-assisted system of claim 1, wherein the control unit is further configured to initialize the registration transform from a seed transform, the seed transform determined based on images captured by the imaging device of the instrument while known relative movements occur between the instrument and the imaging device.

13. The computer-assisted system of claim 1, wherein to update the registration transform based on the determined error, the control unit is configured to:
update the registration transform in response to the error being smaller than a configurable upper limit; or
update the registration transform in response to the error being larger than a configurable lower limit.

14. The computer-assisted system of claim 1, wherein the control unit is further configured to use a magnitude of the error to control a speed at which one or more input controls teleoperate the instrument.

15. The computer-assisted system of claim 14, wherein to control the speed at which the one or more input controls teleoperate the instrument, the control unit is configured to:
set an upper speed for movement of the instrument based on the magnitude; or
set a gain for haptic feedback applied to the one or more input controls based on the magnitude.

16. A method of operating a computer-assisted system, the method comprising:
receiving, by a control unit and from an imaging device, successive images of an instrument mounted to a repositionable arm of a computer-assisted device;
determining, by the control unit and based on the successive images, an observed velocity of a feature of the instrument;
determining, by the control unit, an expected velocity of the feature of the instrument based on kinematics of the repositionable arm;
transforming, by the control unit, the observed velocity, the expected velocity, or both the observed and expected velocities to a common coordinate system using a registration transform;
determining, by the control unit, an error between a direction of the observed velocity and a direction of the expected velocity in the common coordinate system; and
updating, by the control unit, the registration transform based on the determined error.

17. The method of claim 16, further comprising:
controlling, by the control unit, the instrument using the registration transform.

18. The method of claim 16, wherein:
the feature is a point feature of the instrument; and
the observed velocity of the feature comprises a change in position of the point feature in the successive images.

19. The method of claim 16, wherein:
the feature is an alignment feature of the instrument; and
the observed velocity of the feature comprises a change in orientation of the alignment feature in the successive images.

20. The method of claim 16, wherein:
the feature is a feature set comprising a plurality of features; and
the observed velocity of the feature set is an aggregation of observed velocities for the features in the feature set.

21. The method of claim 16, wherein the expected velocity comprises a change in position or a change in orientation of the feature due to movement of one or more input controls used to manipulate the instrument.

22. The method of claim 16, wherein updating the registration transform comprises updating a rotation portion of the registration transform based on the error while not updating a translation portion of the registration transform based on the error.

23. The method of claim 16, further comprising:
using, by the control unit, a magnitude of the error to control a speed at which one or more input controls teleoperate the instrument.

24. A non-transitory machine-readable medium comprising a plurality of machine-readable instructions which when executed by one or more processors associated with a computer-assisted device, are adapted to cause the one or more processors to perform a method comprising:
receiving, from an imaging device, successive images of an instrument mounted to a repositionable arm of a computer-assisted device;
determining an observed velocity of a feature of the instrument based on the successive images;
determining an expected velocity of the feature of the instrument based on kinematics of the repositionable arm;
transforming the observed velocity, the expected velocity, or both the observed and expected velocities to a common coordinate system using a registration transform;
determining an error between a direction of the observed velocity and a direction of the expected velocity in the common coordinate system; and
updating the registration transform based on the determined error.

25. The non-transitory machine-readable medium of claim 24, wherein:
the feature is a point feature of the instrument, and the observed velocity of the feature comprises a change in position of the point feature in the successive images; or
the feature is an alignment feature of the instrument, and the observed velocity of the feature comprises a change in orientation of the alignment feature in the successive images.

26. The non-transitory machine-readable medium of claim 24, wherein updating the registration transform comprises:
updating a rotation portion of the registration transform based on the error while not updating a translation portion of the registration transform based on the error.

* * * * *